US00PP34480P3

(12) United States Plant Patent
Koning

(10) Patent No.: US PP34,480 P3
(45) Date of Patent: Aug. 2, 2022

(54) ***CURIO* PLANT NAMED 'BLUES'**

(50) Latin Name: *Curio ficoides*
Varietal Denomination: Blues

(71) Applicant: Geu Koning, Westerbork (NL)

(72) Inventor: Geu Koning, Westerbork (NL)

(73) Assignee: Koning & Koning B.V., Westerbork (NL)

( * ) Notice: Subject to any disclaimer, the term of this patent is extended or adjusted under 35 U.S.C. 154(b) by 0 days.

(21) Appl. No.: 17/505,452

(22) Filed: Oct. 19, 2021

(65) Prior Publication Data

US 2022/0132718 P1 Apr. 28, 2022

(30) Foreign Application Priority Data

Oct. 27, 2020 (QZ) ..... PBR 2020/2633

(51) Int. Cl.
*A01H 6/14* (2018.01)
*A01H 5/02* (2018.01)
*A01H 6/32* (2018.01)

(52) U.S. Cl.
USPC ..... Plt./480
CPC ..... *A01H 6/32* (2018.05)

(58) Field of Classification Search
USPC ..... Plt./480
CPC ..... A01H 6/14; A01H 5/02
See application file for complete search history.

*Primary Examiner* — Keith O. Robinson
(74) *Attorney, Agent, or Firm* — Penny J. Aguirre

(57) ABSTRACT

A new cultivar of *Curio* plant named 'Blues' that is characterized by its compact plant habit, its very well-branched and compact plant habit, its upright growth habit, its blueish foliage color, and its long leaves with a fine texture.

2 Drawing Sheets

Botanical classification: *Curio ficoides*.
Variety denomination: 'Blues'.

CROSS-REFERENCE TO A RELATED APPLICATION

This application claims priority to European Community Plant Variety Office (CPVO) Plant Breeder's Rights Application No. 2020/2633 filed on Oct. 27, 2020, under 35 U.S.C. 119(f), the entire contents of which is incorporated by reference herein.

BACKGROUND OF THE INVENTION

The present invention relates to a new and distinct cultivar of *Curio* plant, botanically known as *Curio ficoides* 'Blues' and will be referred to hereinafter by its cultivar name, 'Blues'. The new cultivar of *Curio* is an herbaceous perennial grown for container and landscape use.

The new cultivar was derived from a controlled breeding program conducted by the Inventor in Westerbork, The Netherlands. The overall purpose of the breeding program was to develop new cultivars of *Curio* plants with upright, compact, and well-branched growth habits combined with long leaves that are fine in texture and blue in color.

'Blues' arose from a cross made in September of 2015 by the Inventor between *Curio ficoides* 'Mount Everest' (not patented) as the female parent and an unpatented selection from the Inventor's breeding program, designated as accession number S1501K1 as the male parent. 'Blues' was selected as a single unique plant by the Inventor in 2016 in Westerbork, The Netherlands.

Asexual propagation of the new cultivar was first accomplished by cuttings in 2017 by the Inventor in Paterswolde, The Netherlands. Propagation by cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'Blues' as a unique cultivar of *Curio*.

1. 'Blues' exhibits a very well-branched and compact plant habit.
2. 'Blues' exhibits an upright growth habit.
3. 'Blues' exhibits blue foliage color.
4. 'Blues' exhibits long leaves with a fine texture.

The female parent is similar to 'Blues' in having foliage that is blue in color and an upright growth habit. The female parent differs from 'Blues' in having larger leaves that are wider and thicker, a less compact plant habit, and has less branches. The male parent is similar to 'Blues' in foliage color but differs from 'Blues' in having finer leaves and a more compact plant habit. 'Blues' can be most closely compared to *Curio ficoides* 'AMICU1909' (not patented). 'AMICU1909' is similar to 'Blues' in having overall blueish color foliage. 'AMICU1909' differs from 'Blues' in having a shorter plant height, foliage that has a blend of green and grey colors with the blue color, and thicker leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listing by Floranews.

BRIEF DESCRIPTION OF THE DRAWINGS

The accompanying color photographs illustrate the overall appearance and distinct characteristics of the new *Curio*. The plant in the photograph is 1 year in age as grown from 3 cuttings in a 15-cm container in an unheated greenhouse in Waddinxveen, The Netherlands.

The photograph in FIG. 1 provides a view of the plant habit of 'Blues'.

Figure 1:
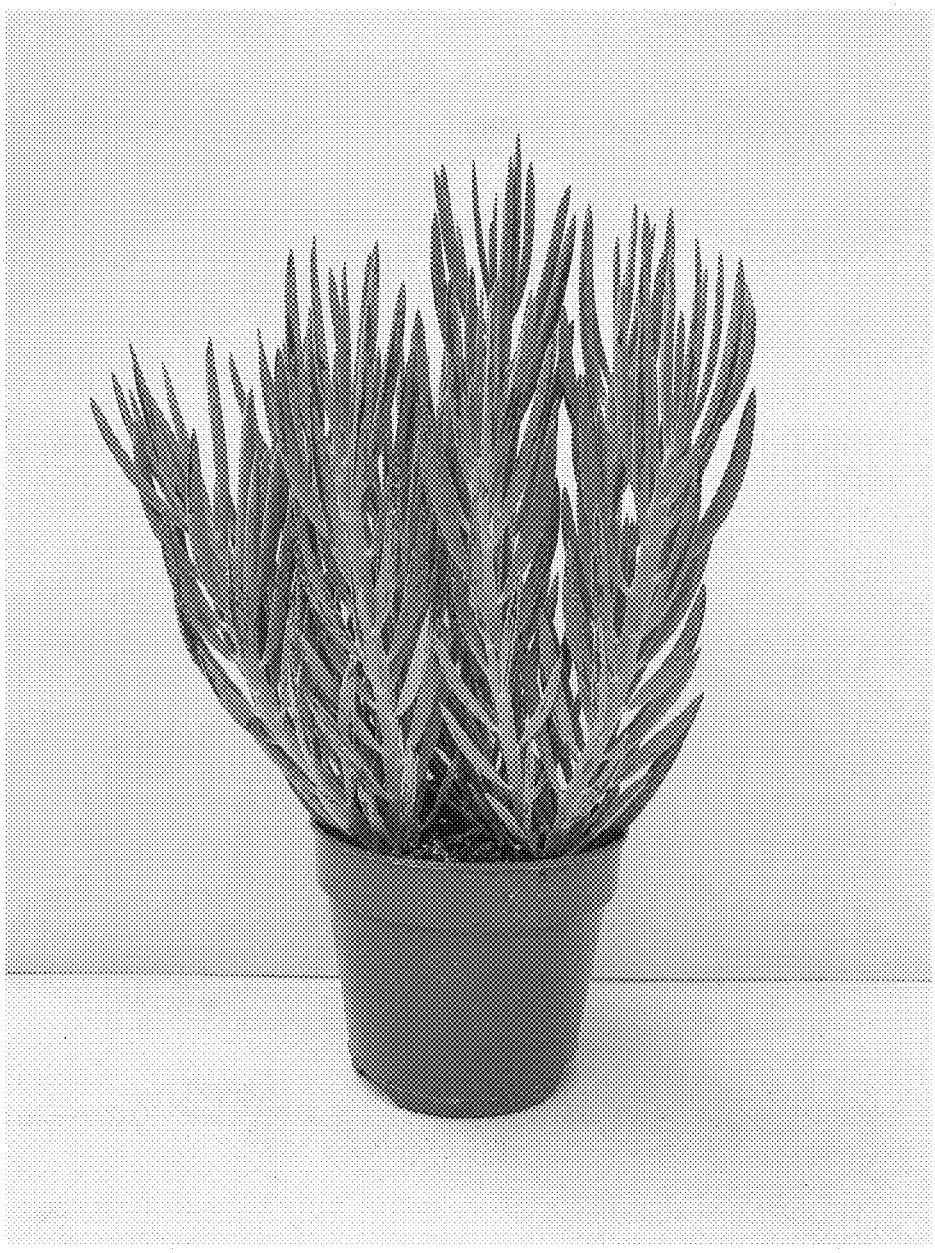
Figure 2:
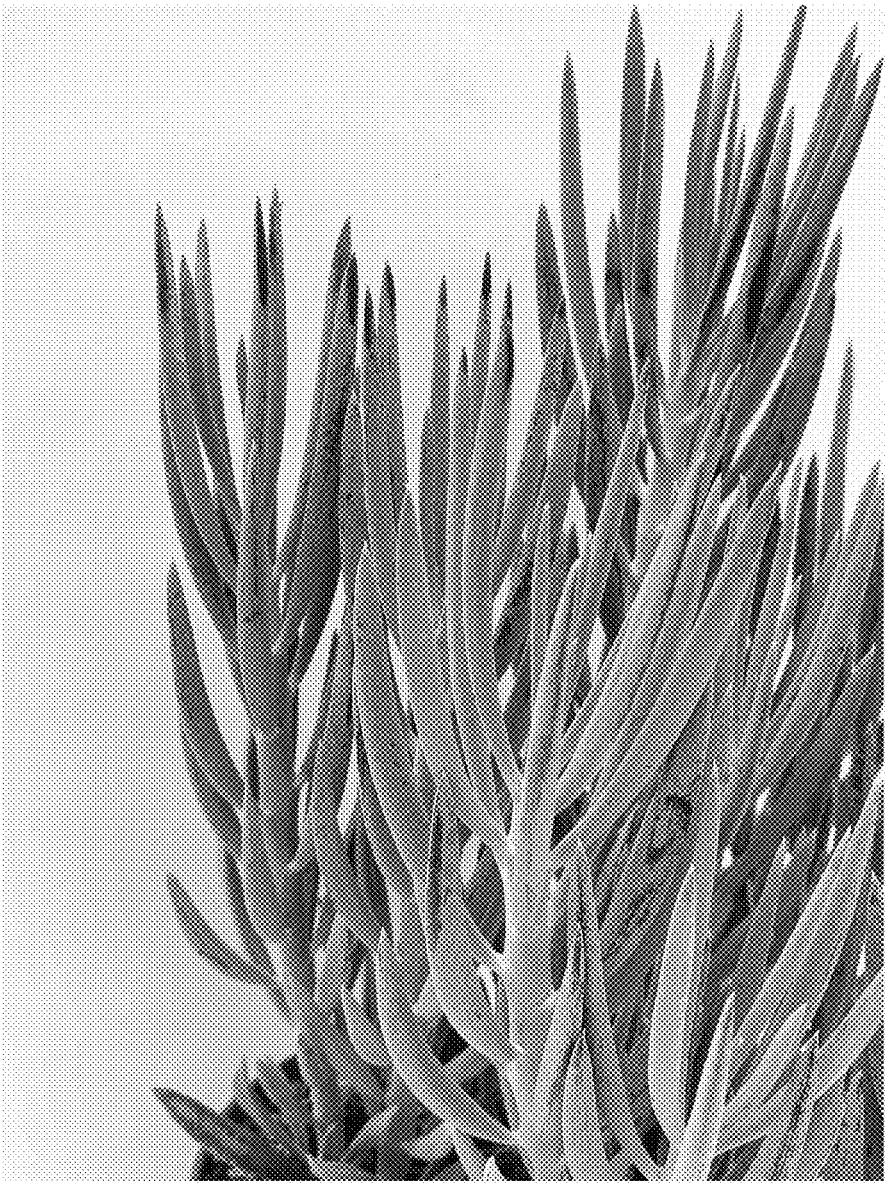

The photograph in FIG. 2 provides a close-up view of the foliage of 'Blues'.

The colors in the photographs may differ slightly from the color values cited in the detailed botanical description, which accurately describe the colors of the new *Curio*.

DETAILED BOTANICAL DESCRIPTION

The following is a detailed description of one-year-old plants grown with 3 cuttings in 15-cm containers in an unheated greenhouse in Erica, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Herbaceous perennial.

*Plant habit.*—Upright, compact.

*Height and spread.*—Reaches about 30 cm in height and 26 cm in width as a one-year-old plant in a 15-cm container.

*Hardiness.*—At least in U.S.D.A. Zones 9a to 11b.

*Diseases and pests.*—No susceptibility to resistance to diseases or pests has been observed.

*Root description.*—Fine, fibrous, 162D in color.

*Propagation.*—Cuttings.

*Growth habit.*—Moderately vigorous.

*Root development.*—Cuttings root in about 20 days and fully develop in 7-cm container in about 25 weeks.

Stem description:

*Shape.*—Round.

*Stem color.*—NN137A with a waxy overlay closest to 188A.

*Stem size.*—Average of 17 cm in length and 1 cm in diameter.

*Internode length.*—An average of 5 mm.

*Stem substance.*—Succulent.

*Stem surface.*—Smooth, glabrous, waxy.

*Branching habit.*—Well-branched, 1 main stem per cutting and an average of 10 lateral stems per container.

Foliage description:

*Leaf shape.*—Ligulate, triangular in diameter.

*Leaf substance.*—Succulent.

*Leaf division.*—Simple.

*Leaf base.*—Cuneate.

*Leaf apex.*—Acute.

*Leaf venation.*—Parallel, upper and lower surface colors match leaf coloration.

*Leaf margins.*—Entire.

*Leaf aspect.*—Slightly curved, upwards, held in an average angle of 70° (90°=vertical).

*Leaf arrangement.*—Whorled.

*Leaf surface.*—All surfaces smooth, glabrous, waxy.

*Leaf color.*—Young upper and lower surface; base 144A, middle to top 137C, waxy layer ranging between 122C and 188A, mature upper and lower surface; base 144A, center to top NN137A, waxy layer ranging between 122C and 188A.

*Leaf size.*—About 7 cm in length, 6 mm in width, 4 mm in depth (thickness).

*Leaf quantity.*—Average of 36 per lateral stem.

*Leaf attachment.*—Sessile.

Inflorescence description: No flowers have been produced to date.

It is claimed:

1. A new and distinct variety of *Curio* plant named 'Blues' as described and illustrated herein.

* * * * *